United States Patent [19]

Korolkov et al.

[11] 4,305,539

[45] Dec. 15, 1981

[54] SURGICAL SUTURING INSTRUMENT FOR APPLICATION OF A STAPLE SUTURE

[76] Inventors: Ivan A. Korolkov, Polyarnaya ulitsa, 52, korpus 2, kv. 174; Viktor S. Saveliev, ulitsa Donskaya, 27, kv. 29; Evgeny G. Yablokov, Rogozhsky val, 6, kv. 45; Georgy V. Astafiev, Rizhsky proezd, 7, kv. 108; Viktor V. Tishin, ulitsa Voronezhskaya, 34, korpus 5, kv. 345; Boris A. Smirnov, ulitsa Borisa Galushkina, 17, kv. 26, all of Moscow, U.S.S.R.

[21] Appl. No.: 112,169

[22] Filed: Jan. 15, 1980

[30] Foreign Application Priority Data

Mar. 26, 1979 [SU] U.S.S.R. ............................... 2747328

[51] Int. Cl.³ .............................................. A61B 17/32
[52] U.S. Cl. ........................................ 227/8; 128/305; 227/109; 227/119; 227/135; 227/19
[58] Field of Search .................. 128/325, 305, 324 R, 128/374 C; 227/DIG. 1, 8, 19, 135, 152, 153, 155, 109, 119

[56] References Cited

U.S. PATENT DOCUMENTS

| | | | |
|---|---|---|---|
| 3,079,606 | 3/1963 | Bobrov et al. | 227/19 X |
| 4,047,654 | 9/1977 | Alvarado | 227/DIG. 1 |
| 4,111,206 | 9/1978 | Vishnevsky et al. | 227/19 X |
| 4,162,678 | 7/1979 | Fedotov et al. | 128/305 |

FOREIGN PATENT DOCUMENTS

| | | | |
|---|---|---|---|
| 2822803 | 12/1978 | Fed. Rep. of Germany | 227/DIG. 1 |
| 1276239 | 6/1972 | United Kingdom | 128/334 R |
| 366858 | 6/1973 | U.S.S.R. | 227/DIG. 1 |

*Primary Examiner*—Paul A. Bell
*Attorney, Agent, or Firm*—Steinberg & Raskin

[57] ABSTRACT

Disclosure is made of a surgical instrument, comprising a supporting body with a replaceable die, a magazine with staples, a carriage-holder, a staple ejector, a carriage-holder mechanical actuator, and a staple ejector mechanical actuator.

The replaceable die is provided with a shaped guide plate corresponding to each of the suture types.

The end surface of the magazine and of the staple ejector are also shaped so as to suit the type of suture being applied and to conform to the shape of a respective die.

4 Claims, 9 Drawing Figures

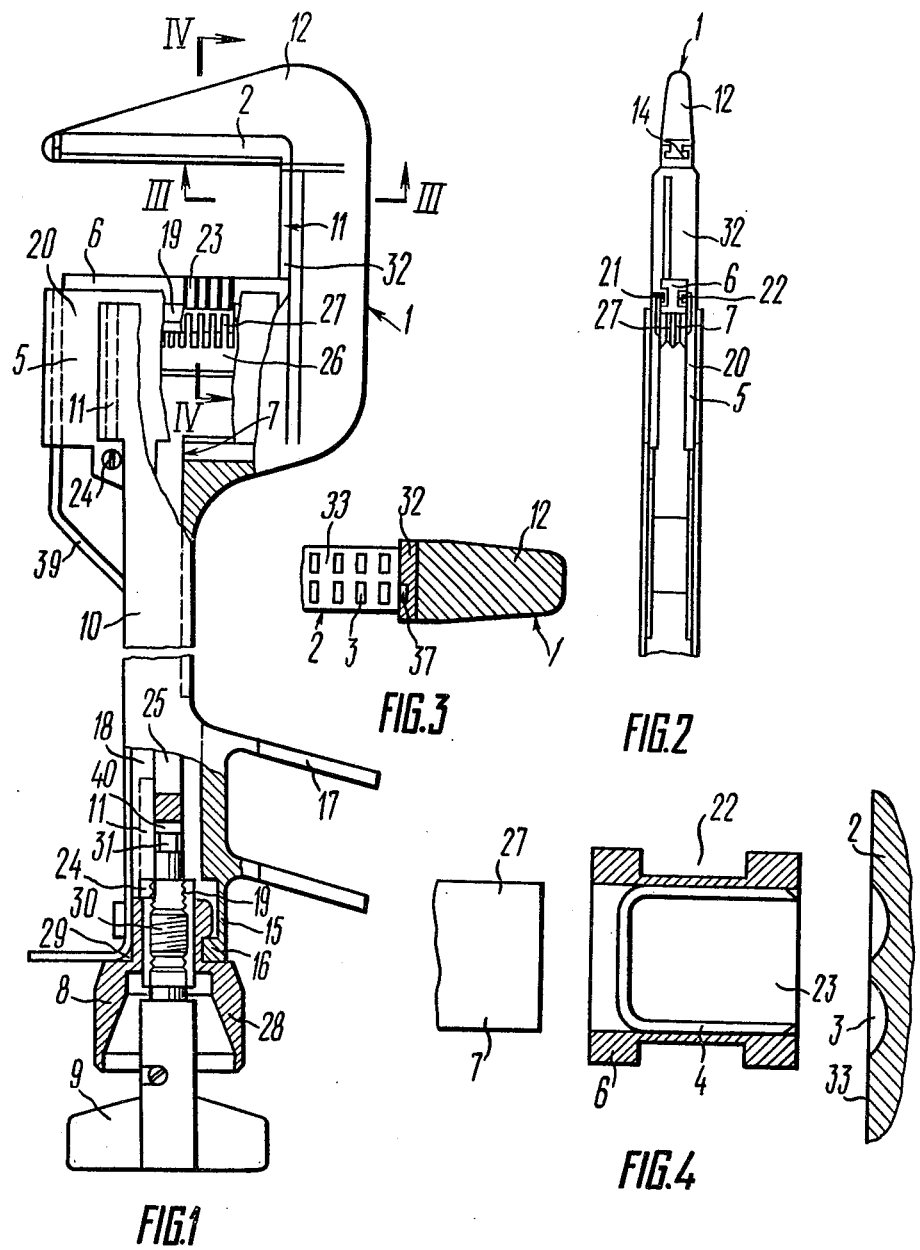

SURGICAL SUTURING INSTRUMENT FOR APPLICATION OF A STAPLE SUTURE

The present invention relates to medical equipment and more particularly to a surgical suturing instrument for application of a staple suture, e.g., when suturing various organs and tissues with metallic staples, especially the stumps of hollow organs, such as blood vessels, intestines, the stomach, the bronchus, pulmonary tissue, and some other organs, as well as for establishing an artificial filter on a blood vessel during operations for thrombus formation.

Up till now a great variety of surgical suture instruments have been developed. Said instruments are designed for suturing (closing) the stumps of hollow organs. As it is known commonly different organs and operative techniques involved in suturing the stumps of hollow organs require the use of different types of sutures to be applied. Thus, for instance, the linear suture is applied for suturing the intestinal stumps, while for suturing the bronchial stump the palisade or the oblique (diagonal) suture is placed; whenever an extra staunch suture is required, the decussate (X-shaped) suture is expedient to be applied. Surgical sutures are also classified by and differ in length and thickness of the tissues being stitched up. Thus, the suture established in stitching up the gastric stump is as long as 120 mm, whereas the suture applied in stitching up the stumps of intestines, the bronchus, or the vascular bundle is up to 40 mm long.

One prior-art surgical suturing instrument for application of a staple suture is heretofore known to use commonly for stitching up various organs and tissues with metallic staples, especially for stitching up the stumps of hollow organs (cf. U.S. Pat. No. 3,079,606).

Another prior art suturing instrument comprises a supporting body with a replaceable die having a number of recesses for the staples to bend, a mechanically actuated carriage-holder with a change magazine, a staple ejector, a mechanical actuator of the carriage-holder and a mechanical actuator of the staple ejector.

The supporting body is an oblong trough provided with guides and a hook to the inner surface of which a replaceable die is held, having a number of recesses for the staples to bend. The carriage-holder with a change magazine is slidable along the guides of the supporting body, and is also provided with guides. The staple magazine has staple slots arranged so as to suit the arrangement of the die recesses. Each of the staple slots is to accommodate a single metallic staple. The staple ejector with prongs is slidable along the carriage-holder guides, the ejector prongs being arranged according to the pattern of the staple slots in the magazine.

The carriage-holder is screw-actuated, while the staple ejector is lever-actuated.

The instrument operates as follows. The hook is brought under the organ being sutured. The carriage-holder along with the staple magazine and ejector is advanced towards the die by rotating the nut of the carriage-holder actuator, with the result that the tissue being sutured is compressed until blood flow is arrested and the so-called suturing gap is defined between the die surface, wherein the opened staple slots are provided, and the staple magazine surface. Then the staple ejector is also advanced towards the die by pressing the ejector actuating lever, with the result that the ejector prongs enter the staple slots to drive the staples out of them.

Metallic staples, after having pieroed the compressed tissue with their legs, catch the die recesses with said legs and thrust thereagainst to be bent into the shape of the letter B, thus uniting the tissue firmly.

However, said instrument is capable of placing a single type of suture only, e.g., the linear suture.

In order to apply all other types of sutures one must have at his disposal such a number of instruments as to apply every type of suture, which results in a considerable amount of surgical equipment involved.

It is the main object of the present invention to provide various types of sutures applied with the use of a single suturing instrument.

It is another object of the present invention to provide a surgical suturing instrument that will preclude any error on the part of surgeon in conforming the die, magazine and staple ejector which would result, at best, in breakage of the instruments, and at worst, in failure of the suture followed by the lethal outcome.

It is one more object of the present invention to cut down the total cost of the equipment (i.e., suturing instruments and accessories) aimed at obtaining a variety of sutures needed in surgical practice.

It is a still further object of the present invention to provide convenience and reliability in using the standardized units of the suturing instrument which require standard manipulations in order to obtain different types of sutures in practical surgery.

Said and other objects are accomplished due to the fact that in a surgical suturing instrument for application of a staple suture, comprising a supporting body with a replaceable die having a number of recesses for bending the staples fed from a change magazine provided with staple slots and mounted on a mechanically actuated carriage-holder, as well as a mechanically-actuated ejector adapted to drive the staples out of the magazine and bring them in engagement with the replaceable die so as to establish a staple suture, according to the invention use is made of a replaceable die and of a magazine for establishing every type of suture, said replaceable die has an end guide plate situated in a plane square with the surface having staple bending recesses and jutting out from the die on its side facing the magazine, and the surface of the guide plate of every replaceable die has a different shape to suit each of the suture types, while the end surface of every change magazine for each type of suture is shaped so as to suit the shape of the guide plate of the die for said type of suture; the staple ejector is also replaceable and its end surface is shaped similarly to the shape of the end of the magazine for the respective type of suture.

Owing to the provision of a replaceable staple ejector and an end guide plate of the die shaped similarly to the shape of the end surfaces of the magazine and ejector, the disclosed instrument assures a positive comformity of the die, ejector and magazine, which makes it possible to obtain different types of sutures with the same instrument, to avoid any surgeon's errors in setting the die, ejector and magazine which correspond to a definite type of suture and hence to obviate failure of the suture applied, as well as cuts down the costs of the equipment adapted for applying diverse types of sutures and adds to the convenience of handling the instrument.

It is expedient that the shaped surface of the guide plate be defined by slots opening towards the magazine, while the magazine and ejector be provided with the respective projections adapted to enter said slots.

In what follows the invention is illustrated in a detailed description of some specific exemplary embodiments thereof with reference to the attached drawings, wherein:

FIG. 1 is a general, fragmentarily cutaway side elevation view of the instrument, according to the invention;

FIG. 2 is a general plan view of the instrument, according to the invention;

FIG. 3 is a section taken along the line III—III in FIG. 1;

FIG. 4 is a section taken along the line IV—IV in FIG. 1;

Figure 6:
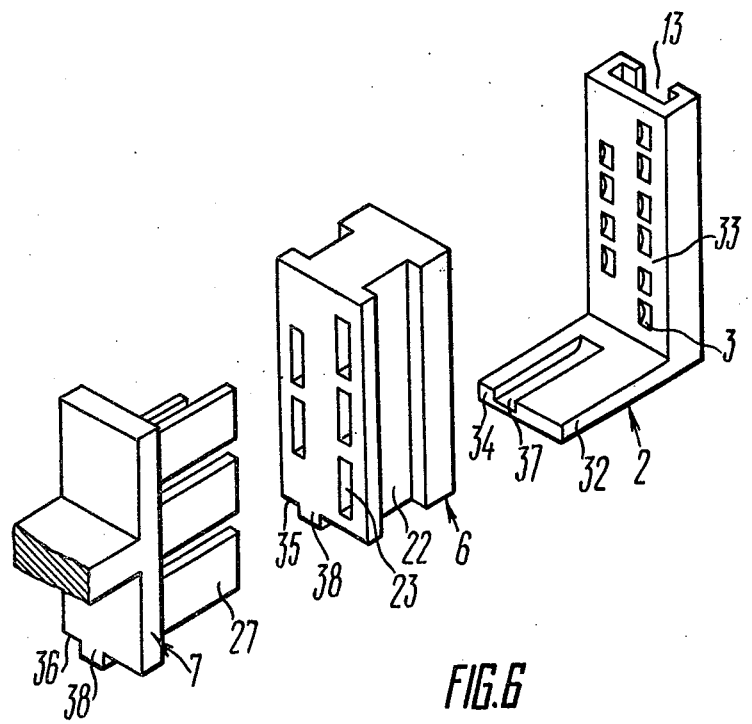
FIG. 6 is a scaled-up perspective view of the ejector, magazine and die for applying the linear suture.

The surgical suturing instrument for application of a staple suture comprises a supporting body 1 (FIG. 1) with a replaceable die 2, wherein a number of recesses 3 (FIGS. 3, 4, 6, 7, 8, 9) are provided for staples 4 (FIG. 4) to bend, a mechanically-actuated carriage-holder 5 (FIG. 1) with a change magazine 6, a staple ejector 7, a mechanical actuator 8 of the carriage-holder, and a mechanical actuator 9 of the staple ejector.

The supporting body is an oblong trough 10 having guides 11 (indicated with a dotted line) and a hook 12 held to the inner surface of which is the die 2. A T-slot 13 (FIGS. 6, 7, 8, 9) is provided in the replaceable die 2 in order to set the latter into the instrument, while a T-shaped projection 14 (FIG. 2) is provided on the inner surface of the hook 12 for the purpose. A tailpiece 15 (FIG. 1) of the supporting body has a lug 16 adapted to interact with the carriage-holder mechanical actuator 8. The supporting body 1 has a grip 17 for convenience in instrument handling.

The mechanically-actuated carriage-holder 5 is shaped as an oblong stem having a tailpiece 18 at one end and a holder 20 carrying the change staple magazine 6, at the other end.

In order to keep the magazine 6 in place on the holder 20 a number of lugs 21 (FIG. 2) are provided on the latter, while the same number of shaped slots 22 are made in the magazine 6 (FIGS. 6, 7, 8, 9). In addition, some through slots 23 for staples are made in the magazine 6, the arrangement pattern of said slots corresponding to that of the recesses 3 in the die. The mechanically-actuated carriage-holder 5 has lugs 24 to interact with the supporting body 1 (FIG. 1). The tailpiece 19 of the carriage-holder is a hollow structure provided with external and internal thread.

The staple ejector 7 is also shaped as an oblong stem 25 having a T-slot (not shown) at one end, and a head 26 with prongs 27, at the other end.

The configuration and arrangement pattern of the prongs 27 of the ejector 7 correspond to those of the staple slots 23 (FIGS. 6, 7, 8, 9).

According to the invention the ejector 7 (FIG. 1) is a replaceable component; to this end, the ejector is detachably joined, through its T-slot, with a T-shaped projection 40 of the mechanical actuator 9 of the ejector 7.

The mechanical actuator 8 of the carriage-holder 5 is in fact a nut 28 having an annular groove 29.

The nut 28 establishes a screw pair along with the external thread of the tailpiece 19, and with its annular groove 29 is slidably engaged with the lug 16 of the supporting body 1. The mechanical actuator 9 of the ejector 7 is essentially a screw 30 having an annular groove 31.

The screw 30 establishes another screw pair along with the internal thread of the tailpiece 19 of the carriage-holder, and with its annular groove 31 is slidably engaged with the yoke (not shown) of the ejector 7.

According to the invention an end guide plate 32 is provided on the replaceable die 2 (FIGS. 6, 7, 8, 9), arranged square with a surface 33, wherein the recesses are made, said guide plate jutting out towards the magazine.

Figure 5:
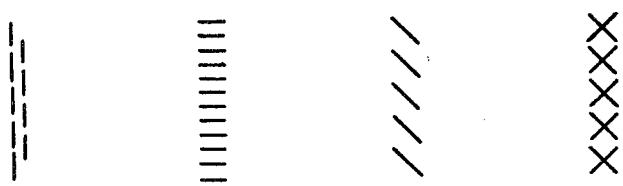
FIG. 5 illustrates conventional symbols of various types of sutures made use of in modern surgery.
Figure 7:
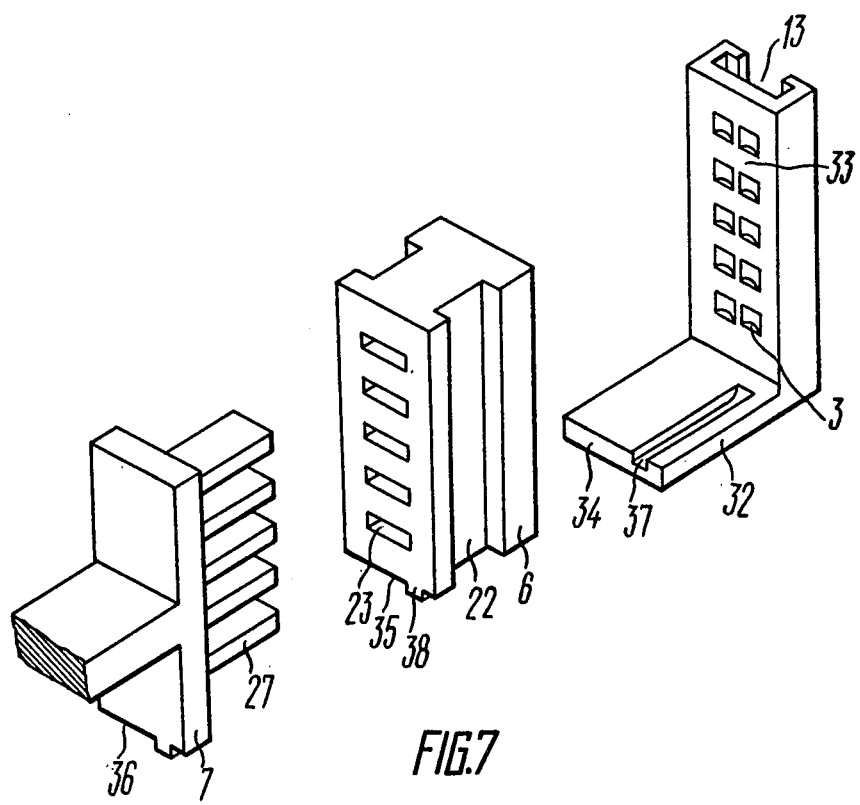
FIG. 7 is a scaled-up perspective view of the ejector, magazine and die for applying the palisade suture.
Figure 8:
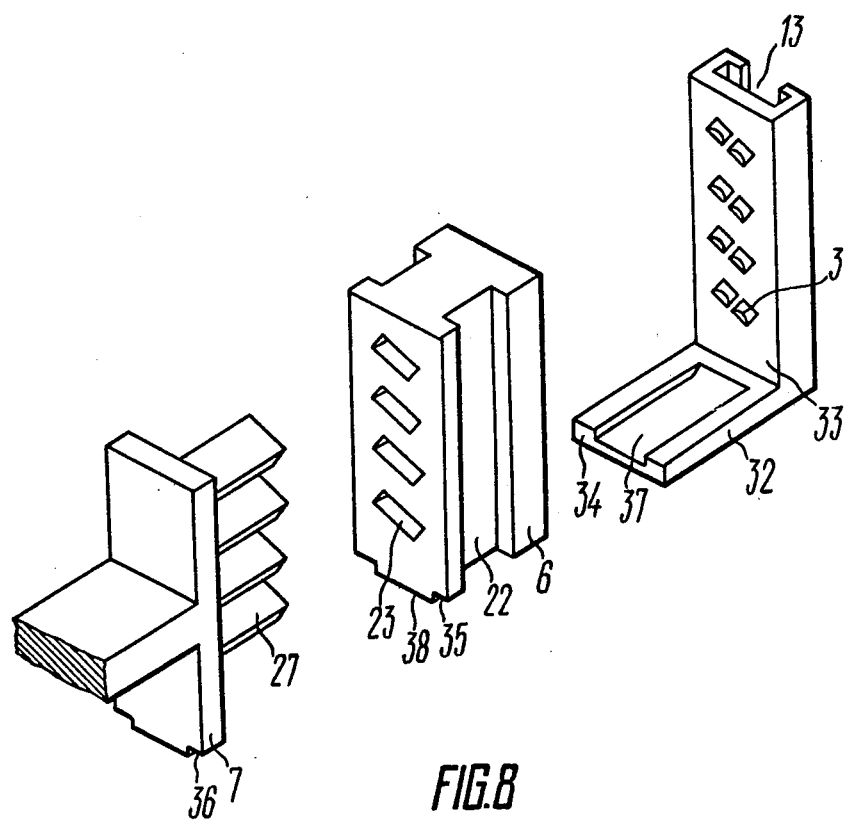
FIG. 8 is a scaled-up perspective view of the ejector, magazine and die for applying the oblique (diagonal) suture.
Figure 9:
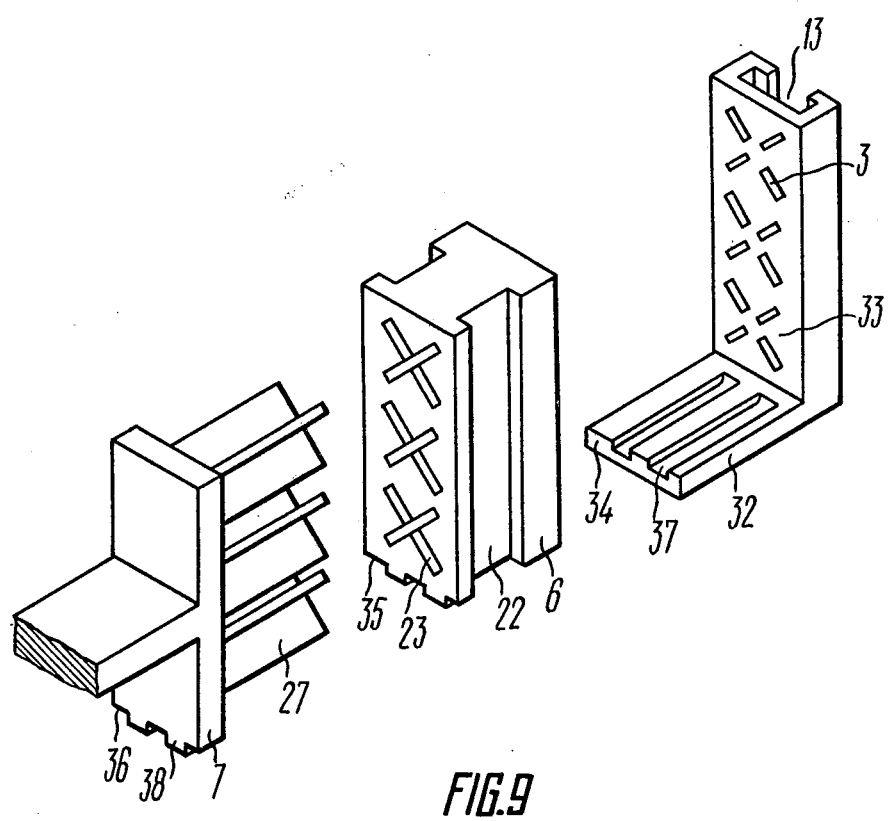
FIG. 9 is a scaled-up perspective view of the ejector, magazine and die for applying the decussate (X-shaped) suture.

The end guide plate 32 has a shape 34 which is imparted only to a definite type of suture (FIG. 5). One of the end surfaces 35 (FIGS. 6, 7, 8, 9) of the magazine 6 and one of the end surfaces 36 of the ejector 7 are shaped so as to suit the shape of the end guide plate 32 for a strictly definite type of suture.

The shape of the end guide plate may be established by slots 37, while the shape of the magazine and ejector ends, by similar lugs 38.

In order to prevent the tissue being sutured from escaping beyond the zone of suture in the course of operation, an extra component is provided in the instrument, viz. a restriction strip 39 (FIG. 1), capable of reciprocating between the hook 12 and and the nut 28.

When applying a staple suture to the intestinal stump the present surgical suturing instrument operates as follows. According to the techniques adoped in the modern surgery the intestinal stump is to be stitched up with the linear suture. Therefore, one must select the appropriate replaceable die 2 (FIG. 6), the change magazine 6 and the replaceable ejector 7. Then the nut 28 (FIG. 1) of the carriage-holder mechanical actuator is rotated counterclockwise to retract the carriage-holder to the initial position, whereupon the carriage-holder is extracted from the supporting body.

The ejector is so set that its T-slot (not shown) should embrace the annular groove 31 of the screw of the ejector mechanical actuator 9 and its head 26 should enter the holder 20; in this case the shaped end surface 36 (FIG. 6) should be directed oppositely to the lug 24 (FIG. 1).

Next the mechanically-actuated carriage-holder 5 along with the ejector 7 is placed in the troughlike portion 10 of the supporting body 1 so that the ejector 7 is at the bottom of said troughlike portion. Then the nut 28 of the mechanical actuator of the carriage-holder is rotated, whereby the lugs 24 engage the guide slots 11 (shown with a dotted line) in the supporting body 1. Thus, a slidable joint is obtained, capable of reciprocating lengthwise from the hook 12 towards the tailpiece 15 of the supporting body 1.

The change magazine 6 (FIG. 2) is fitted into the carriage-holder in such a manner that the lugs 21 should engage the slots 22 in the magazine 6, whereupon the magazine is advanced all the way along the lugs 21.

The die 2 is then fitted onto the hook 12 (FIG. 1) of the supporting body 1 in such a manner that the T-shaped projection 14 (FIG. 2) of the supporting body 1 should engage the slot 13 (FIG. 6) in the die 2 (FIG. 2);

in this case the end guide plate should face the magazine 6. Next the hook of the supporting body is brought under the organ being sutured (i.e., the intestine in this particular case), and the restriction strip 39 (FIG. 1) is advanced towards the hook so that the organ being sutured should be confined within the die 2, the magazine 6, the hook 12 and the restriction strip 39.

Thereupon the nut 28 of the carriage-holder mechanical actuator is rotated to advance the carriage-holder along with the magazine 6 and the ejector 7 towards the die 2, thus compressing the tissue being sutured to define the suturing gap.

This done, the screw 30 of the ejector actuator 9 is rotated clockwise to advance the ejector towards the die, with the result that the ejector prongs 27 enter the staple slots 23 of the magazine 6 to drive the staples out of the magazine slots.

Upon being expelled from the slots the staples pierce with their legs the tissue being sutured, thrust against the die recesses and get bent into the shape of the letter B, thus establishing a suture.

Next the organ being sutured is cut along the plane of the instrument, and the nut 28 of the carriage holder mechanical actuator is rotated counterclockwise to retract the carriage-holder 5 along with the ejector 7 into the initial position. Thus, the organ is released. This terminates the suturing procedure.

In the instrument proposed by the present invention a positive conformity of a replaceable die, magazine and ejector is carried out, whereby any possible errors of medical personnel concerned with setting said change components into the instrument are avoided. This is a feature of paramount importance as otherwise, should any of said components (die, ejector, or magazine) adapted for applying a definite type of suture, e.g., the linear suture be set to operate in conjunction with the change components for applying another type of suture, such as the palisade suture, this will result, at best, in the ejector breakage, while at worst this will lead in wrongly bent staples which in turn might involve subsequently a failure of the suture and an eventual lethal outcome.

Said errors are completely eliminated in the disclosed instrument as should only one of the change components be confused mistakenly the instrument will fail to operate at the very beginning of the suture application procedure, i.e., will fail to compress the tissue being sutured, since the shape of the end guide plate 32 will not mate that of the magazine end surface, which therefore will prevent the mechanically-actuated carriage-holder from being brought together with the die.

Thus, the disclosed instrument is capable of applying different types of sutures, obviates any errors in suture application and hence any possibility of failure of the applied suture, cuts down a total cost of equipment involved in application of diverse types of sutures, and renders the handling and manipulation with the instrument easy and convenient due to unification and standardization of the basic units thereof.

What is claimed is:

1. A surgical suturing instrument comprising:

a supporting body a set of replaceable dies, each of said dies adapted to be supported on said body and having a plurality of recesses for interacting with staples formed in a surface thereof in a particular pattern corresponding to a particular suture and further including a shaped end guide plate extending in the direction of staple ejection situated in a plane substantially normal to the surface in which said recesses are formed, said guide plate having a particular shape corresponding to the respective particular pattern of staple recesses formed in the die;

a set of change magazines, each of said change magazines adapted to be supported on said body and having a plurality of staple slots formed in a particular pattern corresponding to the pattern of a respective die and an end surface having a shape which conforms to the shape of the guide plate of said respective die;

mechanically-actuated carriage holder means for carrying said change magazines and advancing the latter towards said die during the course of a suturing operation; and a set of replaceable staple ejectors, each of said ejectors adapted to be supported on said body and having an end surface having a shape which conforms to the shape of the guide plate of a respective die;

whereby said suturing instrument is capable of applying different types of sutures determined by the respective die, change magazine and staple ejector being utilized.

2. The combination of claim 1 wherein said shaped end guide plate of each of said dies has a slot formed therein having a particular respective configuration and wherein said end surfaces of each of said change magazines and staple ejectors have lugs formed thereon having a particular respective configuration conforming to the shape of a slot of a respective guide plate.

3. The combination of claim 1 further including actuating means for moving said carriage holder means toward said die and actuating means for moving said staple ejectors with respect to said change magazine.

4. The combination of claim 3 wherein each of said actuating means includes a respective screw pair.

* * * * *